(12) United States Patent
Kim et al.

(10) Patent No.: US 6,591,691 B2
(45) Date of Patent: Jul. 15, 2003

(54) APPARATUS FOR AND METHOD OF MEASURING THERMAL STRESS OF CONCRETE STRUCTURE

(75) Inventors: Jin Keun Kim, Taejon (KR); Sang Eun Jeon, Taejon (KR); Kook Han Kim, Changwon (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 1 day.

(21) Appl. No.: 09/829,669

(22) Filed: Apr. 10, 2001

(65) Prior Publication Data

US 2001/0049968 A1 Dec. 13, 2001

(30) Foreign Application Priority Data

May 8, 2000 (KR) ........................................ 2000-24439

(51) Int. Cl.$^7$ .............................................. G01M 15/00
(52) U.S. Cl. ............................................ 73/803; 73/803
(58) Field of Search ............................. 73/8, 9, 73, 74, 73/76, 146, 803, 863

(56) References Cited

U.S. PATENT DOCUMENTS

| | | | |
|---|---|---|---|
| 4,792,912 A | | 12/1988 | Kuramoto et al. |
| 5,129,443 A | * | 7/1992 | Yano et al. ................. 164/4.1 |
| 6,234,008 B1 | * | 5/2001 | Sjoblom et al. ............... 73/73 |

* cited by examiner

Primary Examiner—Kamand Cuneo
Assistant Examiner—Monica D. Harrison
(74) Attorney, Agent, or Firm—Kinney & Lange, P.A.

(57) ABSTRACT

Disclosed are a testing apparatus for and a method of measuring thermal stresses of concrete structures. Overcoming the limitations that conventional analytical access techniques have, the apparatus opens a new way to conveniently measure the thermal stress attributable to the heat of hydration generated in concrete structures indoors. Using a material different in coefficient of thermal expansion from concrete, the apparatus can directly measure the change in thermal stress of the concrete which is subjected to internal and/or external confinement. By using various materials, the thermal stress which varies depending on the confinement extent can be inferred. Additionally, an accurate prediction of the thermal stresses generated actually in concrete can be obtained, reflecting unclear physical properties of early-age concrete.

6 Claims, 7 Drawing Sheets

(a)

(a) Stress change in an outer portion of a concrete structure (b) Stress change in an inner portion of a concrete structure (a) Temperature change  (b) Stress change (a) Temperature change  (b) Stress change (a) Moduli of strain of concrete by use of embedded strain gauge (b) Comparison of stress between using and concrete strains

APPARATUS FOR AND METHOD OF MEASURING THERMAL STRESS OF CONCRETE STRUCTURE

BACKGROUND OF THE INVENTION

1. Field of the Invention

The present invention relates to an apparatus for and a method of measuring thermal stresses attributed to the heat of hydration generated from concrete structures, which can be used in the laboratory instead of conventional analytical techniques or experiments performed on actual concrete structure.

2. Description of the Prior Art

Recently, active research has been directed to the development of cement which is free from generating heat upon hydration because the heat of hydration causes significant problems in constructing massive concrete structures or effecting high strength concretes. A concrete structure undergoes a certain thermal stress caused by the heat of hydration of cement, according to confining conditions given to its inner and outer portions. In extreme cases, the thermal stress may cause cracks in concrete structures to deleteriously affect the utility, water tightness and durability thereof.

It is, therefore, very important to quantitatively examine the influence of the heat of hydration on the degree of thermal stress and the occurrence of cracks. Generally, thermal stresses generated in concrete structures are inferred analytically or experimentally.

For analytical inference, finite element methods are usually employed, in which a variety of construction conditions can be effectively modeled. The experimental method to infer the thermal stress is further broken down into two manners: one is to apply equipments and gauges directly to actual or model structures; and the other is to utilize testing apparatuses for measuring thermal stresses, which are manufactured for laboratory use.

Because it makes assumptions on the behavior of all parameters, the analytical method is apt to give inaccurate results for early-age concrete, whose physical properties cannot be clearly determined. This problem is also not readily solved by the experimental method using actual or model structures. Additionally, the experimental method suffers from the disadvantage of requiring a large expenditure because an experiment must be carried out during the construction.

The testing apparatuses, most of which are manufactured in Germany or Japan, are very expensive and have difficulty in modeling actual thermal stresses generated in concrete structures. Additionally, the apparatuses cannot detect the changes in thermal stress of the structure subjected to internal and external confinements. The change in stress generated from the inside of a structure, which is subjected to internal and external confinements, as shown in FIG. 1a, has a tendency to be opposite to that of the change in the stress generated at the circumferential portion of the structure, which is subjected to internal confinement, as shown in FIG. 1b. Those apparatuses cannot effectively reflect the tendency. Also, the testing apparatuses are economically unfavorable in that additional devices are required to describe the thermal change at some sites of the structure.

One of prior arts is described by Tazawa and Iida (Transaction of the Japan Concrete Institute, Vol. 5, E. Tazawa and K. Iida, pp. 119–126). They suggested a thermal crack testing apparatus which consists of 4 stainless steel pipes and plates fixed to the opposite ends of the pipes via nuts. A strain gauge is equipped on the pipes through which water is circulated at a predetermined temperature. A laboratory in which a sample is placed is suitably controlled for temperature to embody the thermal hysteresis obtained by temperature analysis. A confinement degree is determined according to the change in the stiffness of the pipes and the temperature of the circulating water.

After performing an experiment under semi-adiabatic conditions, Breitenbucher (Material and Structures, Vol. 23, R. Breitenbucher, pp. 172–177) introduced a cracking frame which is designed to arbitrarily control the temperature of the concrete by embedding a copper pipe in a form.

A temperature stress testing machine was disclosed in Proceedings of the International RILEM Symposium, 1994, R. Springenschmid and R. Breitenbucher, pp. 137–144, which is identical in overall mechanical design and shape to the cracking frame, but different in that thermal stress is measured through a load cell equipped on one cross-head portion while concrete dislocation is controlled by use of a step motor.

The conventional techniques described above, however, differ from the invention in technical constitution.

SUMMARY OF THE INVENTION

It is an object of the present invention to provide a testing apparatus which can conveniently measure thermal stresses generated in concrete structures indoors.

It is another object of the present invention to provide a testing apparatus for measuring thermal stresses of concrete structures, which can account for the effect of the internal and external confinements in concrete structures by use of a material different in coefficient of thermal expansion from concrete.

It is a further object of the present invention to provide a method of measuring thermal stresses of concrete structures, which can take accurate account of the effect of the temperature on the thermal stresses by testing in a temperature and humidity chamber with a temperature hysteresis obtained in a certain portion of the concrete structures.

BRIEF DESCRIPTION OF THE DRAWINGS

The above and other objects, features and other advantages of the present invention will be more clearly understood from the following detailed description taken in conjunction with the accompanying drawings, in which.

PREFERRED EMBODIMENTS OF THE INVENTION

Figure 1:
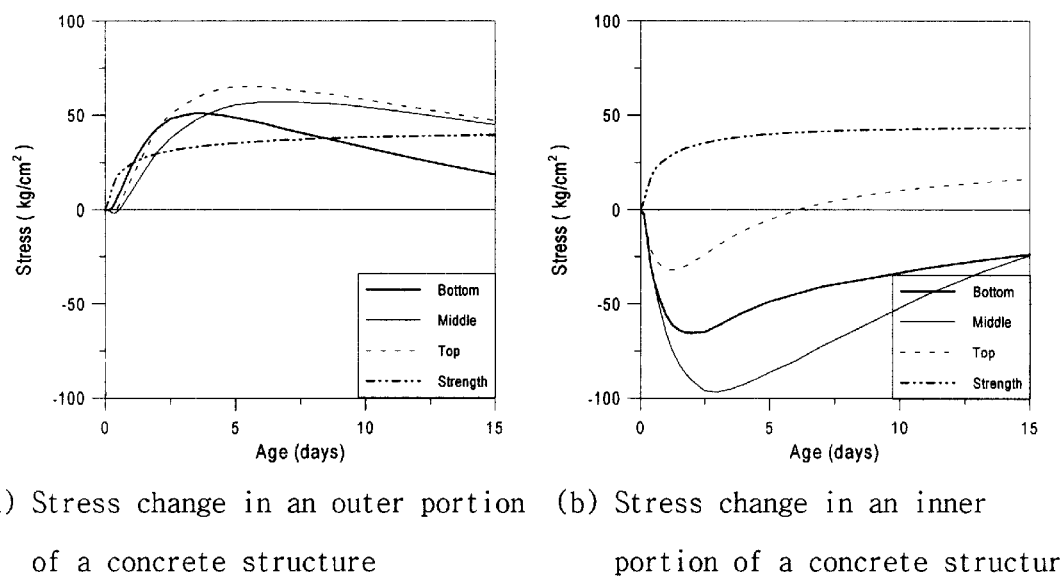
FIG. 1 shows curves in which stresses generated in the outer portion (a) and the inner portion (b) of a concrete structure are plotted against time.

The application of the preferred embodiments of the present invention is best understood with reference to the accompanying drawings, wherein like reference numerals are used for like and corresponding parts, respectively.

Figure 2:
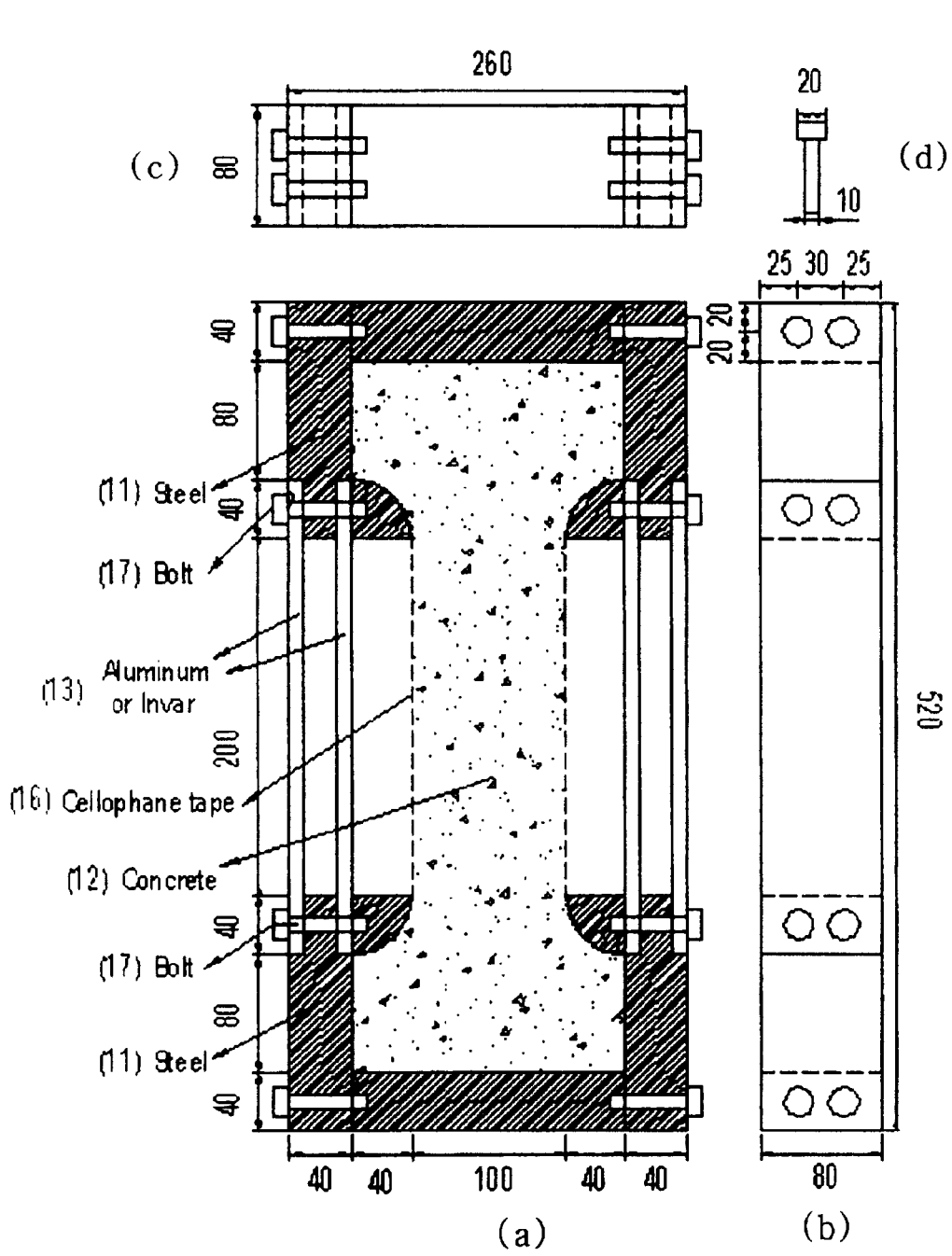
FIG. 2 shows a testing apparatus for measuring thermal stresses of concrete structures in a cross sectional view (a), in a side view (b), and in a plan view (c), and a bolt used in the testing apparatus.

With reference to FIG. 2, a testing apparatus designed according to the present invention is shown in a cross sectional view (a), in a side view (b) and in a plan view (c). FIG. 2d shows a screw used in the testing apparatus. As seen in FIG. 2, the testing apparatus is largely broken down into two parts: steel cross-heads 11 and a metal plate 13 which connects the steel cross-heads 13 to each other. The steel cross-heads 11 are designed in a T form for the apparatus to behave in an integrated manner while the connecting metal plate is made of a material different in coefficient of thermal expansion from the concrete. For instance, invar and aluminum may be exemplified as materials having coefficients of thermal expansion smaller and larger than that of the concrete, respectively.

As seen in FIG. 2, the chief feature of the testing apparatus resides in the metal plate 13 situated between the steel cross-heads 11. If the metal plate 13 has a coefficient of thermal expansion of zero or a coefficient of heat conduction of zero, a complete confinement state of the concrete may be described. In consideration of the existence of no materials which show such properties, metal plates with different coefficients of thermal expansion are recruited to effectively simulate internal and external confinements in the concrete. When the coefficient of thermal expansion of the metal plate employed is smaller than that of the concrete, the concrete is subjected to a compressive stress with an increase of temperature and to a tensile stress with a decrease of temperature. The reverse phenomenon occurs when the metal plate has a coefficient of thermal expansion larger than that of the concrete. In consequence, the thermal stress in the outer portion subjected to the internal confinement can be described by use of a metal plate larger in coefficient of thermal expansion than the concrete and the thermal stress in the inner portion subjected to the internal and external confinements does by a metal plate smaller.

Physical properties of the materials used in the thermal stress testing apparatus of the present invention are given in Table 1, below.

TABLE 1

Physical Properties of Materials

| Material | Coeffi. of Thermal Expansion (× $10^{-6}$/° C.) | Elastic Modulus (× $10^5$ kgf/cm$^2$) |
| --- | --- | --- |
| Concrete | 10 | 3.00 |
| Steel | 11 | 21.0 |
| Aluminum | 24 | 7.33 |
| Invar | 4.5 | 2.89 |

Below, a description will be given of an experimental method with the testing apparatus of FIG. 2 employing the materials shown in Table 1.

Experiment Method

Figure 3:
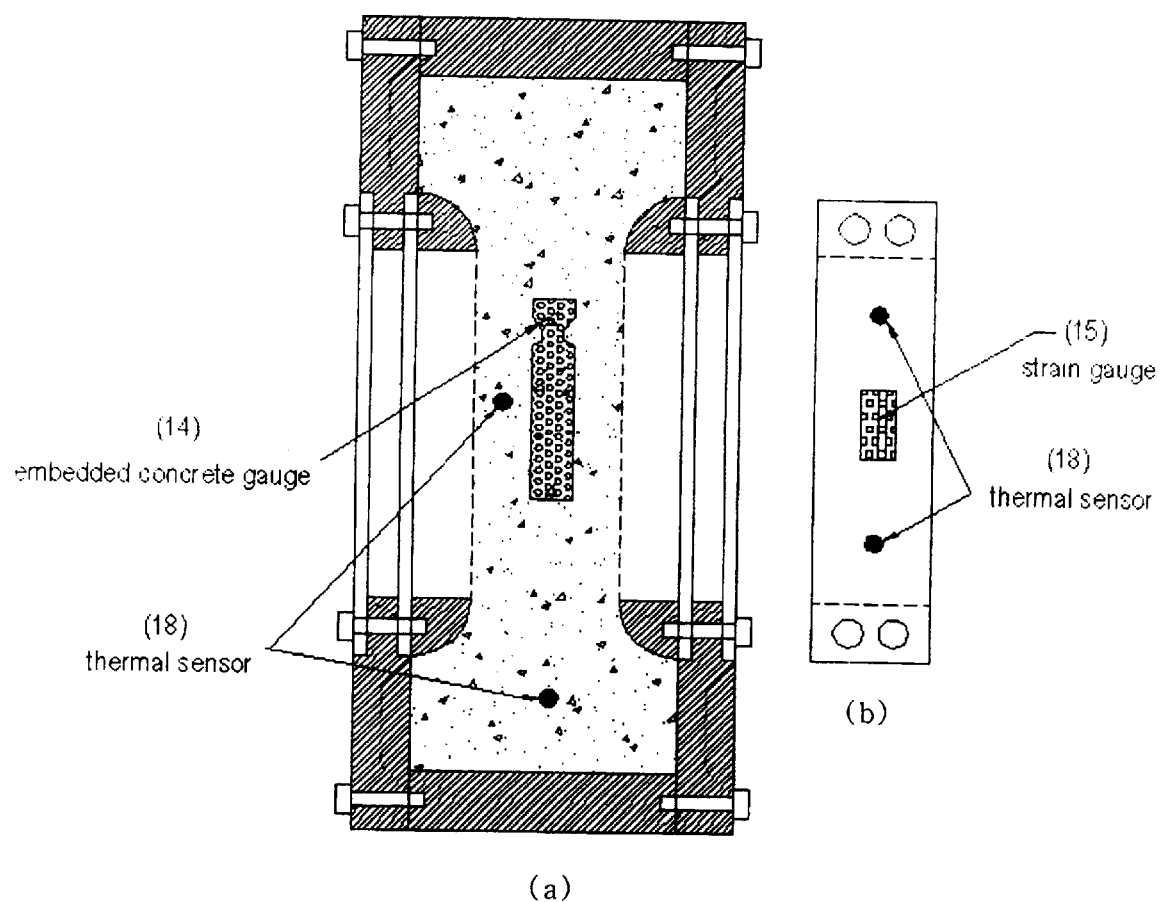
FIG. 3 shows a testing apparatus for measuring thermal stresses of concrete structures, equipped with a strange gauge and temperature sensors, in a cross sectional view (a) and in a side view (b).

With reference to FIG. 3, a testing apparatus filled with concrete is shown in a cross sectional view (a) and in a side view (b). To measure the change in thermal stress of the concrete, as shown in FIG. 3, the testing apparatus is equipped with some meters. That is, a proper strain gauge 15 is attached to the metal plate with a concrete gauge 14 being embedded in the concrete. Thermal sensors 18 are provided inside the concrete and a temperature and humidity chamber to fit the concrete temperature into the programmed temperature. To prevent the concrete from undergoing plastic shrinkage and drying shrinkage, the chamber is programmed to keep its humidity at 85%. In addition, because the amount of the concrete to be applied to the apparatus is not large and the thickness of the applied concrete is only 80 mm, as seen in FIG. 2, the heat of hydration generated from the applied concrete 12 is too small to affect the concrete 12 when account is taken of the thermal exchange which actively occurs in the portion exposed directly to air. A cellophane tape is attached to the concrete boundary indicated by dashed lines in FIG. 3 and detached therefrom after 6 hours of testing. Prior to testing, a thin steel plate which supports the testing apparatus is coated with a sufficient amount of grease and oil to prevent the generation of friction or to greatly reduce the extent of friction, if occurring. A preexperiment in which many bearings were employed in lieu of a plate, showed that no friction influenced the measurement of thermal stresses.

Figure 4:
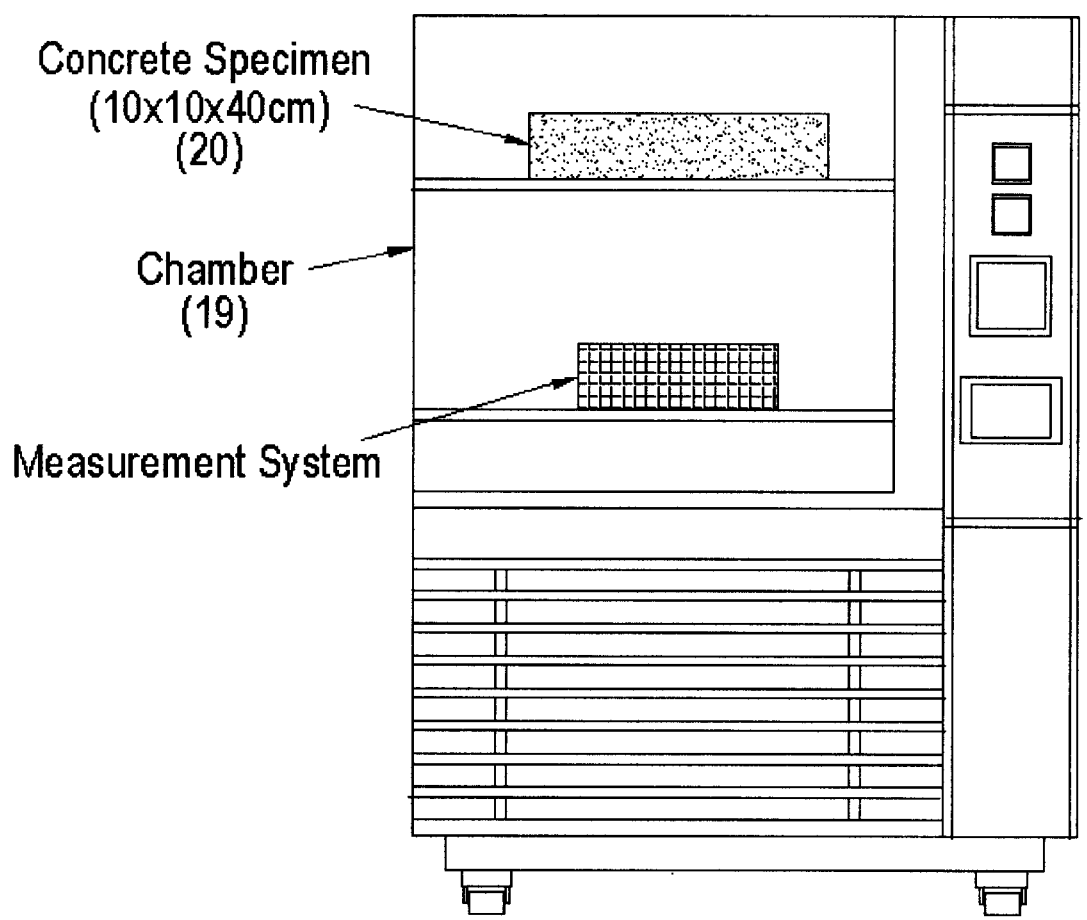
FIG. 4 shows a temperature and humidity chamber in which the testing apparatus is placed.
Figure 5:
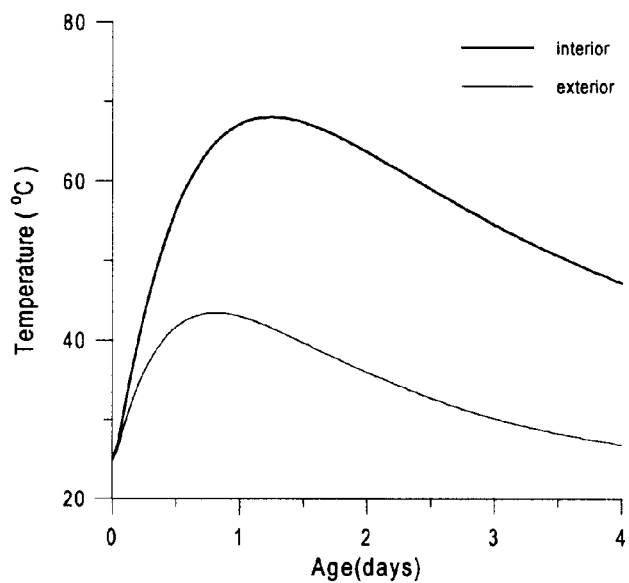
FIG. 5 is a graph showing temperature hystereses used in an experiment.
Figure 6:
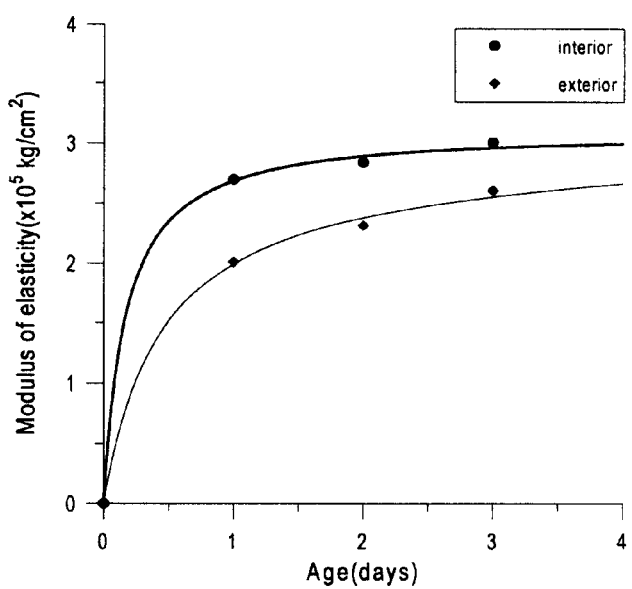
FIG. 6 shows curves in which moduli of elasticity are plotted for confinement conditions against time.

To predict the thermal stress of a target structure, temperature analysis should be conducted preferentially. Through an analysis program, a concrete sample is analyzed for temperature as shown in FIG. 5, after which an experiment is made in a temperature and humidity chamber 19 shown in FIG. 4, which is programmed to maintain the same temperature states as the analyzed temperature hysteresis. FIG. 6 shows temperature hystereses analyzed according to confining conditions.

Measuring the strain attributed to a temperature change requires very precise experiments. In this regard, for the concrete to have the same temperature as an analyzed one upon placing, materials, such as the testing apparatus, aggregate, water, etc., are placed for one day before the placing, in a chamber whose temperature and humidity are set to values of the initial stage. However, even though the materials are controlled in temperature to the initial value, the concrete, the testing apparatus and the chamber may have different temperatures after the application owing to outer temperatures or other factors upon placing. To avoid this problem, the chamber is set at the initial temperature for 6 hours after the placing, thereby maintaining all of the testing apparatus, the concrete and the chamber at the same temperature. Thereafter, the temperature profile of the chamber is accounted for in the same manner as the temperature hysteresis obtained through the temperature analysis.

Measurement of Thermal Stress and Analysis

From the data obtained in the above experiment, the stresses exerted upon the concrete structure can be calculated on the following theoretical basis.

If the strain is completely confined, the stress of the concrete may be expressed by the formula 1:

$$f_{c,res} = E_c \epsilon_{c,free} \tag{1}$$

wherein, $f_{c,res}$ is the thermal stress of the concrete upon complete confinement;

$E_c$ is the elastic modulus of the concrete, and $\epsilon_{c,free}$ is the strain of the concrete in a free state.

However, since the concrete is not subjected to complete confinement, the stress can be expressed by the following formula 2:

$$f_c = E_c(\epsilon_{c,free} - \epsilon_c) \quad (2)$$

wherein, $f_c$ is the stress of the concrete within the frames, $\epsilon_c$ the strain of the concrete within the frames.

Because a force equilibrium is established between the concrete and the frames, there can be obtained the following formula 3:

$$A_s E_s(\epsilon_{c,free} - \epsilon_s) = A_c E_c(\epsilon_c - \epsilon_{c,free}) \quad (3)$$

Wherein, $A_s$ and $A_c$ are cross sectional areas of the frame material and the concrete, respectively; and $E_s$ and $E_c$ are elastic moduli of the frame material and the concrete, respectively.

Here, the substitution of the formula 2 into the formula 3 and the rearrangement thereof gives the following formula 4:

$$f_C = \frac{A_S}{A_C} E_S (\varepsilon_{S,free} - \varepsilon_S) \quad (4)$$

In the formula 4, $A_s$, $A_c$, and $E_s$ are known constants, and $\epsilon_{s,free}$ can also be obtained by the following formula 5:

$$\epsilon_{s,free} = \alpha_s \Delta T \quad (5)$$

wherein, $\alpha_s$ is the coefficient of thermal expansion of the frame material, and $\Delta T$ is a change in temperature.

Therefore, if the strain ($\epsilon_s$) of the frame is measured at a certain time, the stress of a concrete structure at that time, whether it is in the early-age or not, can be immediately calculated irrespective of the composition of the concrete.

Assay for Reliability of the Testing Apparatus

To verify the testing reliability of the apparatus of the present invention, an examination was made of physical properties of the concrete while conducting the experiment. FIG. 6 depicts the changes in elastic modulus of the concrete formulations obtained through the experiment. As seen in FIG. 6, the assay was conducted largely to quantify two phenomena. Because the thermal behavior of an inner portion was examined in a different manner from that of an outer portion, the inner and the outer portions were separately expressed after the application of respective temperature hystereses.

To monitor whether the temperature hysteresis applied through the temperature and humidity chamber could accurately exert itself on the concrete and the metal plate, a temperature sensor 18 was provided for the concrete and the metal plate, each, while measuring the strain by use of a strain gauge.

Figure 7:
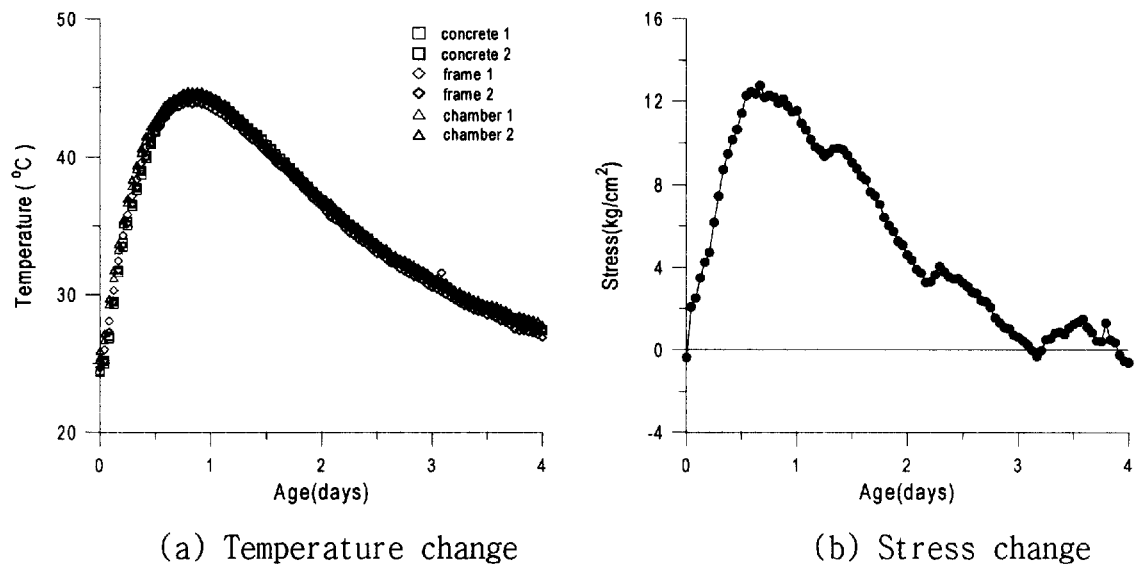
FIG. 7 shows curves obtained by use of an aluminum plate, in which the temperature (a) and the stress (b) of the concrete are plotted against time.
Figure 8:
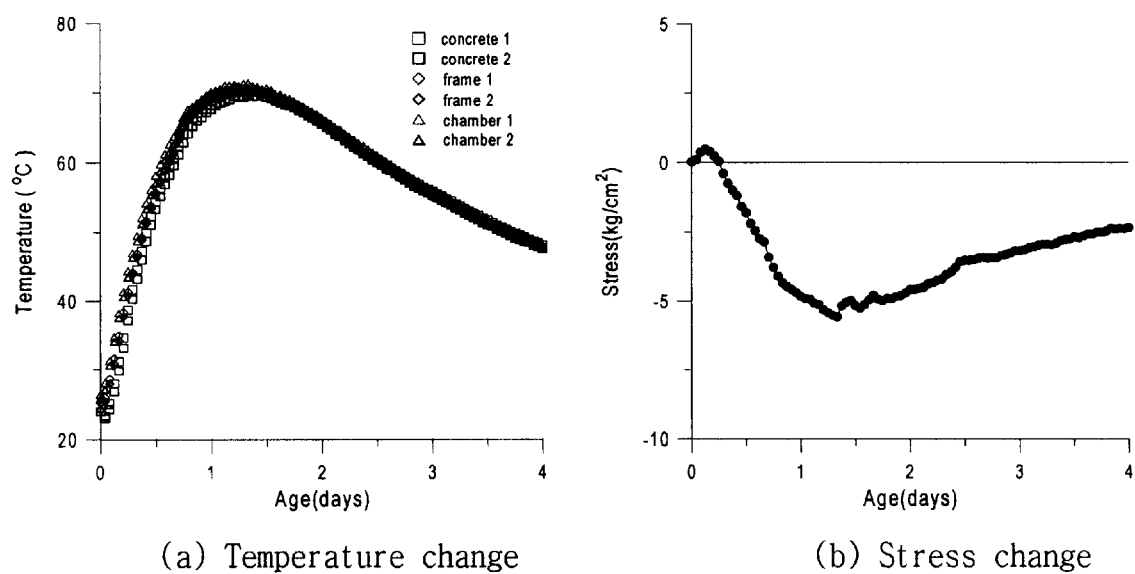
FIG. 8 shows curves obtained by use of an invar plate, in which he temperature (a) and the stress (b) of the concrete are plotted against time.

With reference to FIGS. 7 and 8, there are shown experimental data obtained through the testing apparatus recruiting aluminum greater in coefficient of thermal expansion than concrete and invar smaller in coefficient of thermal expansion than concrete, respectively. The curves depicted according to the data in FIGS. 7 and 8 account for the stress changes of the outer portion and the inner portion, respectively. In addition, as seen from the temperature change in each experiment, the programmed temperatures (chamber 1 and 2), the temperatures within the concrete (concrete 1 and 2), and the temperatures of the apparatus (frame 1 and 2) all vary within a very narrow error range (±1° C.).

Figure 9:
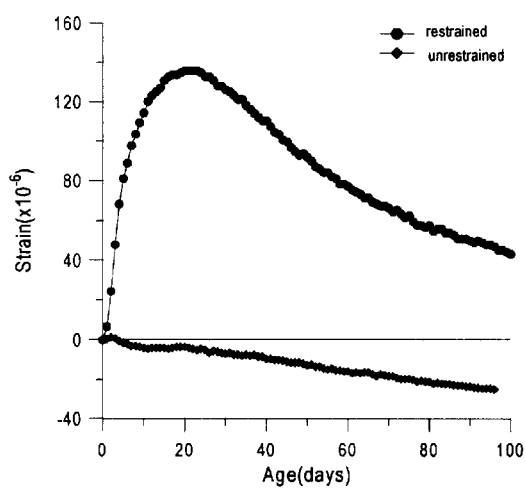
FIG. 9 shows curves demonstrating the reliability of the testing apparatus of the present invention, in which the moduli of strain of the concrete measured from embedded gauges are plotted against time (a) and the stresses of a concrete sample, calculated from the results of embedded gauges and the strain of plate, are compared.
Figure 9:
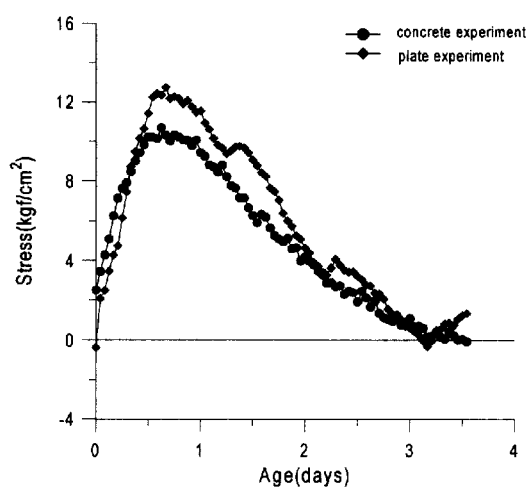

For comparison with the stress of the concrete obtained by use of the testing apparatus (denoted as 'plate experiment'), stress was calculated on the basis of the strain measured directly by use of the embedded concrete gauge (denoted as 'concrete experiment') (FIG. 9).

As described hereinbefore, a testing apparatus is provided for conveniently measuring the thermal stresses generated in massive concrete structures. With the applicability to early-age concrete whose physical properties cannot be clearly determined, the apparatus can give an accurate prediction of the thermal stresses actually generated in concrete.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An apparatus for measuring thermal stresses of concrete structures, comprising:

an upper steel frame and a lower steel frame, each having a T form;

a metal plate for connecting the upper steel frame to the lower steel frame to form a housing which confines concrete therein, said metal plate being jointed to the steel frames by bolts; and cellophane tape applied to the inside of the structure to prevent the leakage of the concrete confined therein.

2. The apparatus as set forth in claim 1, wherein said metal plate is different in coefficient of thermal expansion from concrete.

3. The apparatus as set forth in claim 2, wherein said metal plate is made of invar with a smaller coefficient of thermal expansion than that of concrete or of aluminum with a greater coefficient of thermal expansion than that of concrete.

4. A method of measuring thermal stresses of concrete structures by use of the apparatus of claim 1, comprising the steps of:

setting the apparatus in a temperature and humidity chamber, said apparatus being filled with concrete and equipped with a strain gauge on the frame and with an concrete gauge embedded in the concrete;

controlling the temperatures within the concrete and the temperature and humidity chamber to match the behavior pattern of a pre-analyzed temperature hysteresis; and measuring the strain of the concrete according to the temperature hysteresis.

5. The method as set forth in claim 4, wherein the apparatus, the concrete and the chamber are all maintained at a humidity of 85% to prevent the plastic shrinkage and drying shrinkage of the concrete.

6. The method as set forth in claim 4, wherein the measuring step utilizes the temperature hysteresis obtained when the apparatus, the concrete and the chamber are all maintained at the same temperature.

* * * * *